US008642828B2

(12) United States Patent
Heida et al.

(10) Patent No.: US 8,642,828 B2
(45) Date of Patent: Feb. 4, 2014

(54) PROCESS FOR PURIFYING A RECYCLE STREAM FROM A 1,3-BUTADIENE PROCESSING PLANT

(71) Applicants: Bernd Heida, Ellerstadt (DE); Randolf Hugo, Dirmstein (DE)

(72) Inventors: Bernd Heida, Ellerstadt (DE); Randolf Hugo, Dirmstein (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/732,668

(22) Filed: Jan. 2, 2013

(65) Prior Publication Data
US 2013/0197292 A1    Aug. 1, 2013

Related U.S. Application Data

(60) Provisional application No. 61/582,504, filed on Jan. 3, 2012.

(51) Int. Cl.
*C07C 7/08* (2006.01)
(52) U.S. Cl.
USPC ............................. 585/810; 585/802; 585/809
(58) Field of Classification Search
None
See application file for complete search history.

(56) References Cited

U.S. PATENT DOCUMENTS

| 2,983,772 | A | * | 5/1961 | Mooneyhan et al. | 585/847 |
| 3,798,132 | A | | 3/1974 | Sarno | |
| 7,226,527 | B2 | * | 6/2007 | Bohner et al. | 203/2 |
| 2010/0298621 | A1 | | 11/2010 | Bridges et al. | |
| 2013/0150610 | A1 | * | 6/2013 | Moerbe et al. | 558/338 |

FOREIGN PATENT DOCUMENTS

| WO | WO 2010/134955 A1 | 11/2010 |
| WO | WO 2011/110562 A1 | 9/2011 |

OTHER PUBLICATIONS

U.S. Appl. No. 13/736,446, filed Jan. 8, 2013, Heida, et al.
International Search Report Issued Apr. 16, 2013 in PCT/EP2013/050002 (with English translation of Categories of Cited Documents).

* cited by examiner

*Primary Examiner* — Tam M Nguyen
(74) *Attorney, Agent, or Firm* — Oblon, Spivak, McClelland, Maier & Neustadt, L.L.P.

(57) ABSTRACT

Secondary streams in 1,3-butadiene processing plants still contain high amounts of valuable 1,3-butadiene. An energy-efficient process for purifying a recycle stream from a 1,3-butadiene processing plant is provided. The recycle stream is divided into two substreams: the first substream for prepurifying pure 1,3-butadiene feedstream by removing high boilers relative to 1,3-butadiene in a stripping column and the second substream in an extractive distillation plant.

11 Claims, 1 Drawing Sheet

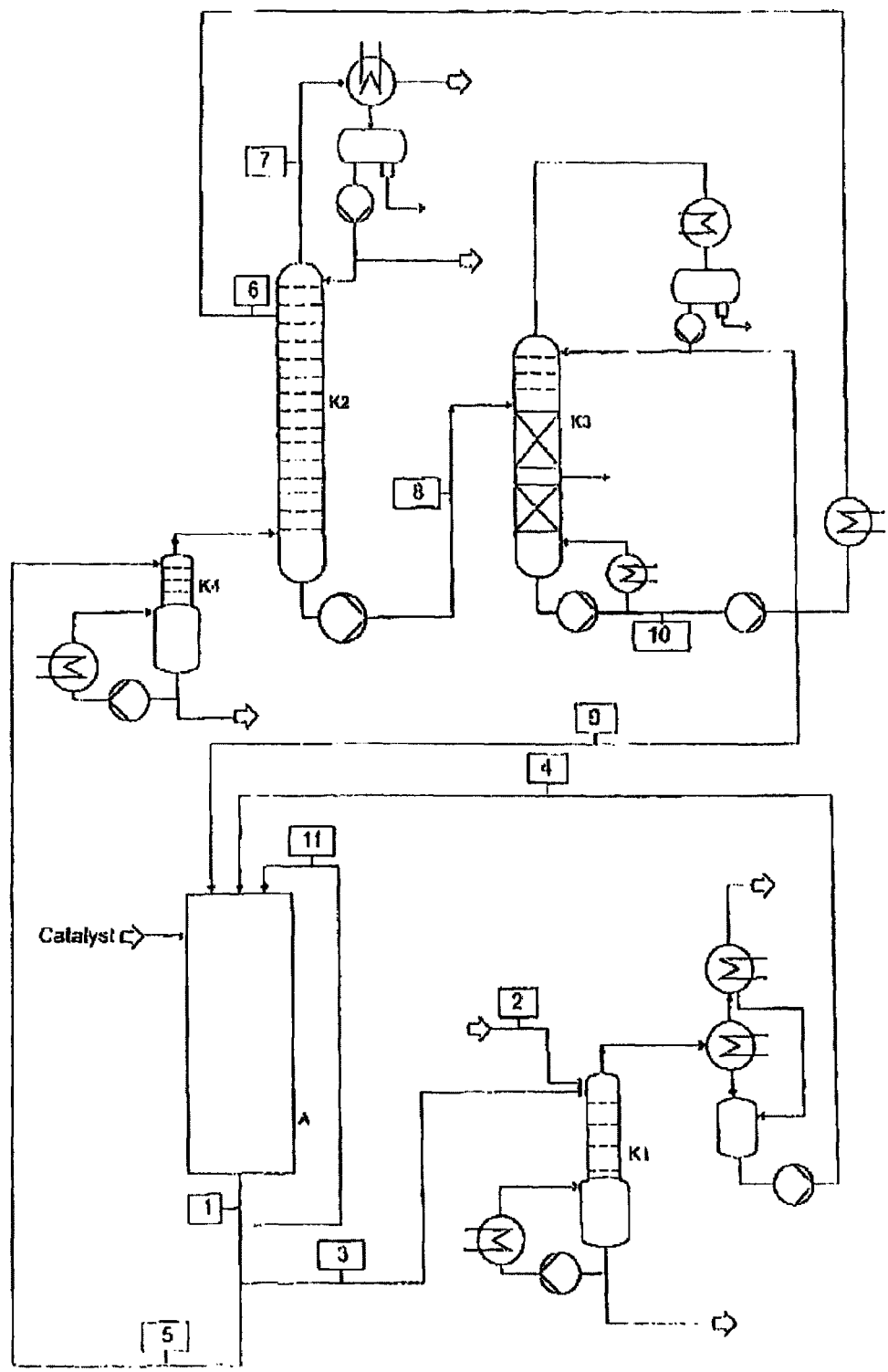

PROCESS FOR PURIFYING A RECYCLE STREAM FROM A 1,3-BUTADIENE PROCESSING PLANT

The invention relates to a process for purifying a recycle stream from a 1,3-butadiene processing plant.

In 1,3-butadiene processing plants, secondary streams are frequently obtained, which still have high contents of the 1,3-butadiene product of value. These streams have to date been worked up externally or disposed of.

It was therefore an object of the invention to provide a process which enables purification of secondary streams from 1,3-butadiene processing plants which still have high contents of 1,3-butadiene product of value in a manner which is simple in terms of process technology and energetically advantageous, to such an extent that polymerizable 1,3-butadiene is obtained which meets the specification requirements for the feed stream into the 1,3-butadiene processing plant, such that it can be used itself as a recycle stream in the plant. The process is additionally also advantageous in environmental respects.

The solution consists in a process for purifying a recycle stream from a 1,3-butadiene processing plant, comprising
- 70-99% by weight of 1,3-butadiene, based on the total weight of the recycle stream,
- 0.1-10% by weight of low boilers relative to 1,3-butadiene, based on the total weight of the recycle stream, and
- 0.1-20% by weight of high boilers relative to 1,3-butadiene, based on the total weight of the recycle stream, where the sum of 1,3-butadiene, low boilers and high boilers in the recycle stream is 100% by weight and the starting material is a pure 1,3-butadiene feed stream having a 1,3-butadiene content of greater than or equal to 98% by weight of 1,3-butadiene, based on the total weight of the pure 1,3-butadiene feed stream, which is subjected beforehand to a prepurification for removal of high boilers relative to 1,3-butadiene in a stripping column and is then supplied to the 1,3-butadiene processing plant, which comprises
- dividing the recycle stream into two substreams, specifically into
- a first substream which is purified in the stripping column for prepurification of the pure 1,3-butadiene feed stream to obtain a first purified recycle stream also comprising the prepurified pure 1,3-butadiene feed stream, and
- a second substream which is purified in an extractive distillation plant by extractive distillation with a selective solvent, said extractive distillation plant comprising
- a main scrubber which is a rectifying column and to which are fed in a liquid form the second substream of the recycle stream in a lower region and the selective solvent in an upper region, the selective solvent flowing through the main scrubber in countercurrent to the second substream of the recycle stream and becoming laden with the 1,3-butadiene, and from which a top stream comprising butanes and butenes is discharged, and
- an outgasser column to which the bottom stream from the main scrubber is supplied, and from which a second purified recycle stream overhead, and a bottom stream comprising purified selective solvent are drawn off, and the first purified recycle stream and the second purified recycle stream being recycled into the 1,3-butadiene processing plant, with the proviso that the recycle stream is divided in such a way that a maximum flow rate is accounted for by the first substream while complying with the specifications for the sum of all streams fed into the 1,3-butadiene processing plant, of a proportion of 1,3-butadiene of greater than or equal to 90% by weight, based on the total weight of all $C_4$ hydrocarbons from the sum of all streams fed into the 1,3-butadiene processing plant.

It has been found that it is possible to work up a recycle stream from a 1,3-butadiene processing plant, which still comprises a relatively high proportion, in the range from 70 to 99% by weight, of 1,3-butadiene, in a manner which is favorable in terms of process technology, such that a maximum substream thereof is purified in a simple manner, in a stripping column, to remove high boilers, and the much more complex purification by extractive distillation using a selective solvent is required only for the residual substream, which is kept to a minimum size. The division into the two substreams is undertaken such that the specifications for the feed stream into the 1,3-butadiene processing plant are met.

The recycle stream, which is obtained as a secondary stream from a 1,3-butadiene processing plant, comprises typically between 70 and 99% by weight of 1,3-butadiene, based on the total weight of the recycle stream, 0.1 to 20% by weight of low boilers relative to 1,3-butadiene, based on the total weight of the recycle stream, 0.1 to 20% by weight of high boilers relative to 1,3-butadiene, based on the total weight of the recycle stream, where the sum of 1,3-butadiene, low boilers and high boilers in the recycle stream is 100% by weight.

The 1,3-butadiene content in the recycle stream is preferably in the range from 80 to 95% by weight, based on the total weight of the recycle stream.

Low boilers relative to 1,3-butadiene in the present case are especially $C_1$ to $C_3$ hydrocarbons.

As low boilers relative to 1,3-butadiene, the recycle stream comprises especially methane, preferably in a proportion of greater than or equal to 90% by weight, based on the total weight of the low boilers relative to 1,3-butadiene.

A pure 1,3-butadiene feed stream is understood in the present case to mean a stream which has a 1,3-butadiene content of greater than or equal to 98% by weight, based on the total weight of the pure 1,3-butadiene feed stream.

Further preferably, pure 1,3-butadiene is understood to mean commercial pure butadiene having at least 99.0% by weight of 1,3-butadiene or else at least 99.4% by weight of 1,3-butadiene, or else at least 99.75% by weight of 1,3-butadiene, based in each case on the total weight.

Before being supplied to the 1,3-butadiene processing plant, this is subjected to a prepurification for removal of high boilers relative to 1,3-butadiene in a stripping column.

The stripping column is preferably operated at elevated pressure, especially in the range from 3.5 to 6.0 bar absolute. The stripping column is preferably equipped with separating internals, especially with trays.

According to the invention, this stripping column already present for the prepurification of the pure 1,3-butadiene feed stream, in addition to the pure 1,3-butadiene feed stream, is also supplied with a substream of maximum size from the recycle stream from the 1,3-butadiene processing plant. This stream too, like the pure 1,3-butadiene feed stream as well, is supplied in the upper region of the stripping column. For this purpose, the column merely has to be adjusted to the higher throughput.

The remaining, second portion of the recycle stream is supplied to a simplified extractive distillation plant, in which the purification thereof is performed with addition of a selective solvent. The extractive distillation plant is simplified in that it is normally sufficient to supply the second substream of the recycle stream to a main scrubber which is in the form of a rectifying column, dispensing with a stripping section.

The second substream of the recycle stream is fed to the main scrubber in the lower region, and the selective solvent in the upper region thereof. From the main scrubber, a top stream comprising butanes and butenes is discharged and a bottom stream comprising a 1,3-butadiene laden selective solvent is drawn off.

The main scrubber is configured as a distillation column with a number of theoretical plates, which may vary significantly with the solvent used and the required purities of the 1,3-butadiene. There may typically be 5 to 50, more preferably 12 to 30, theoretical plates.

The top pressure in the main scrubber is preferably in the range from 3.5 to 6.0 bar absolute. The temperature at the top of the column in the main scrubber is preferably in the range from 20 to 40° C.

The outgasser column is operated at lower pressure relative to the main scrubber.

The selective solvents used in the extractive distillation are preferably the customary solvents known for the removal of 1,3-butadiene.

Suitable selective solvents for the process according to the invention are, for example, butyrolactone, nitriles such as acetonitrile, propionitrile, methoxypropionitrile, ketones such as acetone, furfurol, N-alkyl-substituted lower aliphatic acid amides such as dimethylformamide, diethylformamide, dimethylacetamide, diethylacetamide, N-formyl-morpholine, N-alkyl-substituted cyclic acid amides (lactams) such as N-alkyl-pyrrolidones, especially N-methylpyrrolidone. In general, N-alkyl-substituted lower aliphatic acid amides or N-alkyl-substituted cyclic acid amides are used. Particularly advantageous solvents are dimethylformamide, acetonitrile, furfurol, and especially N-methylpyrrolidone.

However, it is also possible to use mixtures of these solvents with one another, for example of N-methylpyrrolidone with acetonitrile, mixtures of these solvents with cosolvents such as water and/or tert-butyl ethers, for example methyl tert-butyl ether, ethyl tert-butyl ether, propyl tert-butyl ether, n- or isobutyl tert-butyl ether.

N-Methylpyrrolidone is particularly suitable, preferably in aqueous solution, especially with 8 to 10% by weight of water, more preferably with 8.3% by weight of water.

According to the invention, the recycle stream from the 1,3-butadiene processing plant is divided between the two component plants for workup in such a way that the substream which is purified merely by distillation together with the prepurification of the pure 1,3-butadiene feed stream in a stripping column is of maximum size, and the second, residual substream is selected merely of such a size as to comply with the specification requirements for the sum of all streams (feed streams) fed into the 1,3-butadiene processing plant.

The workup of the second substream is more technically and energetically demanding than the workup of the first substream, since this involves an extractive distillation. However, this extractive distillation plant too is simplified in accordance with the invention relative to the prior art: the main scrubber to which the substream of the recycle stream is supplied in countercurrent to the selective solvent, the selective solvent becoming laden with 1,3-butadiene, is, in accordance with the invention, in the form of a rectifying column, which means that the second substream of the recycle stream supplied as a feed stream to the main scrubber is supplied to the main scrubber in the lower region thereof. The main scrubber thus does not have a stripping section.

If required, the extractive distillation plant, in a particular embodiment, may have a stripping column which is connected upstream of the main scrubber and is for removal of high boilers from the second substream of the recycle stream prior to the supply thereof to the main scrubber.

The outgasser column of the extractive distillation plant is preferably configured such that the second purified recycle stream, which is drawn off via the top thereof, has a 1,3-butadiene content of >96% by weight, preferably of >99.5% by weight, based on the total weight of the second purified recycle stream.

The stripping column is preferably configured such that the high boilers are removed down to a residual content of not more than 1000 ppm from the first purified recycle stream, which is drawn off via the top thereof.

In a further preferred process variant, a further substream is removed from the recycle stream from the 1,3-butadiene processing plant and is recycled into the 1,3-butadiene processing plant without prepurification.

This substream is preferably larger than half of the overall recycle stream.

The 1,3-butadiene processing plant is especially a plant for polymerization of 1,3-butadiene or for copolymerization of 1,3-butadiene with one or more comonomers.

Comonomers are especially styrene and/or acrylonitrile.

The polymerization or copolymerization of the 1,3-butadiene may especially be a solution polymerization.

The solution polymerization can especially be performed in the presence of toluene or hexane as a solvent.

The distillative removal of 1,3-butadiene from a mixture comprising $C_4$ hydrocarbons is difficult in terms of process technology because the boiling points of the $C_4$ hydrocarbons differ only slightly from one another. Only by addition of a selective solvent is the separation generally made possible with an acceptable level of complexity.

It is therefore all the more surprising that the inventive process regime can achieve purification and recycling of streams which are obtained in 1,3-butadiene processing plants and meet the prerequisite that the sum of the streams fed into the 1,3-butadiene processing plant have a 1,3-butadiene content of 90% by weight, by supplying a substream of maximum size to a conventional distillation, which is simple in terms of process technology and not very energy-demanding, in a stripping column.

The calculations which follow illustrate the considerable potential for energy saving of the process regime according to the invention compared to the conventional procedure:

For this purpose, the consumption was calculated in kJ/kg of 1,3-butadiene worked up by different process variants:

Specific Energy Consumption According to the Prior Art:

According to the prior art (conventional extractive distillation), already including substantial heat integration, the specific energy consumption is 3898 kJ/kg of 1,3-butadiene. An additional factor is the heat of vaporization for 1,3-butadiene of approx. 370 kJ/kg, so the total is 4268 kJ/kg.

Specific Energy Consumption by the Process According to the Invention:

For the workup of the first substream (in accordance with the invention) in stripping column K1 (without reboiler), only the heat of vaporization for 1,3-butadiene of approx. 370 kJ/kg is required.

For workup of the second substream (in accordance with the invention) in a simplified extractive distillation plant with a main scrubber as the rectifying column, 386 kJ/kg are required for the prevaporization, plus 2039 kJ/kg for the extractive distillation in the main scrubber and in the outgasser column, so that the total is 2425 kJ/kg. Some of the heat (about 70%) can be recovered by heat integration. This leaves 619 kJ/kg for the extractive distillation. There are additionally 386 kJ/kg for the prevaporization. In total, for this process variant, approx. 1000 kJ/kg are required, i.e. less than one quarter compared to a conventional extractive distillation.

By, in accordance with the invention, apportioning a maximum proportion of the recycle stream to the first substream, the energy consumption in the process according to the invention is correspondingly much lower than one quarter of the consumption in a conventional extractive distillation.

The invention is illustrated hereinafter by a drawing.

FIG. 1 shows the schematic diagram of a preferred plant for performance of the process according to the invention.

A 1,3-butadiene processing plant (A) is supplied with a 1,3-butadiene feed stream (2), which has been supplied beforehand to a prepurification in a stripping column (K1), from which high boilers are discharged via the bottom.

From the 1,3-butadiene processing plant (A), a recycle stream (1) is drawn off, which is divided into a first substream (3), which is likewise supplied to the stripping column (K1), from which high boilers are discharged and from which a top stream is drawn off, the latter being fed as the first purified recycle stream (4) to the 1,3-butadiene processing plant (A).

From the recycle stream (1), a second substream (5) is drawn off, which is supplied to an extractive distillation plant. In the preferred embodiment shown in FIG. 1, the second substream (5) of the recycle stream (1) is supplied beforehand to a stripping column (K4) for removal of high boilers and then to the main scrubber (K2) which is in the form of a rectifying column, in the lower region thereof. The main scrubber (K2) is supplied with selective solvent (stream 6) in the upper region thereof.

Via the top of the main scrubber (K2), a stream (7) comprising butanes and butenes is drawn off and discharged.

The bottom stream from the main scrubber (K2) is supplied to the outgasser column (K3), from which a bottom stream (10) comprising purified selective solvent is drawn off and is recycled into the main scrubber (K2), and a top stream from which a second purified recycle stream (9) is recycled into the 1,3-butadiene processing plant.

In the preferred process variant shown in FIG. 1, a third substream of the recycle stream (1) is envisaged, stream 11, which is recycled directly, without further purification, into the 1,3-butadiene processing plant (A).

The invention claimed is:

1. A process for purifying a recycle stream from a 1,3-butadiene processing plant (A), comprising:
   70-99% by weight of 1,3-butadiene, based on a total weight of the recycle stream;
   0.1-10% by weight of low boilers relative to 1,3-butadiene, based on the total weight of the recycle stream; and
   0.1-20% by weight of high boilers relative to 1,3-butadiene, based on the total weight of the recycle stream,
   wherein a sum of the 1,3-butadiene, low boilers, and high boilers in the recycle stream is 100% by weight and a starting material is a pure 1,3-butadiene feedstream comprising a 1,3-butadiene content of greater than 98% by weight of the 1,3-butadiene, based on a total weight of the pure 1,3-butadiene feedstream, which is subjected beforehand to a prepurification for removal of the high boilers in a stripping column and is then supplied to the 1,3-butadiene processing plant (A), the process comprising:
   dividing the recycle stream into
   a first substream which is purified in the stripping column for prepurification of the pure 1,3-butadiene feedstream, thereby obtaining a first purified recycle stream comprising a prepurified form of the pure 1,3-butadiene feedstream, and
   a second substream which is purified in an extractive distillation plant by extractive distillation with a selective solvent, the extractive distillation plant comprising
   a main scrubber which is a rectifying column and to which are fed in a liquid form the second substream of the recycle stream in a lower region and the selective solvent in an upper region, the selective solvent flowing through the main scrubber in countercurrent to the second substream of the recycle stream and becoming laden with the 1,3-butadiene, and from which a top stream comprising butanes and butenes is discharged, and
   an outgasser column to which a first bottom stream from the main scrubber is supplied, and from which a second purified recycle stream overhead, and a second bottom stream comprising purified selective solvent are drawn off, and
   the first purified recycle stream and the second purified recycle stream being recycled into the 1,3-butadiene processing plant (A),
   with the proviso that the recycle stream is divided in such a way that a maximum flow rate is accounted for by the first substream while complying with the specifications for the sum of all streams fed into the 1,3-butadiene processing plant (A), of a proportion of 1,3-butadiene of greater than or equal to 90% by weight, based on the total weight of all $C_4$ hydrocarbons from a sum of all streams fed into the 1,3-butadiene processing plant (A).

2. The process according to claim 1, wherein the recycle stream is divided such that the first substream is larger than the second substream.

3. The process according to claim 1, wherein the 1,3-butadiene processing plant (A) is a plant for polymerization of 1,3-butadiene or for copolymerization of 1,3-butadiene with a comonomer.

4. The process according to claim 3, wherein the comonomer is styrene, acrylonitrile, or a combination thereof.

5. The process according to claim 1, wherein the recycle stream comprises methane as the low boilers in a proportion of ≥90% by weight, based on a total weight of further low boilers relative to 1,3-butadiene.

6. The process according to claim 3, wherein the polymerization or copolymerization of the 1,3-butadiene is a solution polymerization, carried out in the presence of toluene or hexane as a solvent.

7. The process according to claim 1, wherein the stripping column is configured such that the high boilers are removed down to a residual content of not more than 1000 ppm from the first purified recycle stream, which is drawn off via a top thereof.

8. The process according to claim 1, wherein the outgasser column is configured such that the second purified recycle stream which is drawn off via the top thereof has a 1,3-butadiene content of greater than or equal to 96% by weight, based on a total weight of the second purified recycle stream.

9. The process according to claim 1, wherein the extractive distillation plant further comprises a stripping column which is connected upstream of the main scrubber and removes the high boilers from the second substream of the recycle stream.

10. The process according to claim 1, wherein a further substream is removed from the recycle stream and is recycled without prepurification into the 1,3-butadiene processing plant (A).

11. The process according to claim 10, wherein the further substream is larger than half of the recycle stream.

* * * * *